United States Patent [19]
Markussen et al.
[11] Patent Number: 4,661,452
[45] Date of Patent: Apr. 28, 1987

[54] ENZYME CONTAINING GRANULATES USEFUL AS DETERGENT ADDITIVES

[75] Inventors: Erik K. Markussen; Arne D. Fog, both of Vaerlose, Denmark
[73] Assignee: Novo Industri A/S, Denmark

[21] Appl. No.: 738,421
[22] Filed: May 28, 1985
[30] Foreign Application Priority Data
May 29, 1984 [DK] Denmark ............................ 2635/84
[51] Int. Cl.⁴ ........................ C12N 9/98; C11D 3/386
[52] U.S. Cl. ................................ 435/187; 252/174.12
[58] Field of Search ........................ 435/187, 219-225; 252/174.12

[56] References Cited
U.S. PATENT DOCUMENTS
4,106,991 8/1978 Markussen et al. ................ 435/187

FOREIGN PATENT DOCUMENTS
1297461 11/1972 United Kingdom .
1362365 8/1974 United Kingdom .
1554482 10/1979 United Kingdom .

*Primary Examiner*—Lionel M. Shapiro
*Attorney, Agent, or Firm*—Fidelman, Wolffe & Waldron

[57] ABSTRACT

Enzyme containing granulates containing less than 2% chloride and besides enzyme, coating materials, granulating aids and water, more than 35% w/w of a filler system consisting of from 5-70% w/w of the granulate composition of one or more water soluble sulphates, and 5-70% w/w water insoluble salts, especially sulphates, carbonates, phosphates or silicates. The granulates exhibit an excellent storage stability and a satisfactory physical strength.

13 Claims, 6 Drawing Figures

ENZYME CONTAINING GRANULATES USEFUL AS DETERGENT ADDITIVES

BACKGROUND OF THE INVENTION

Figure 1:
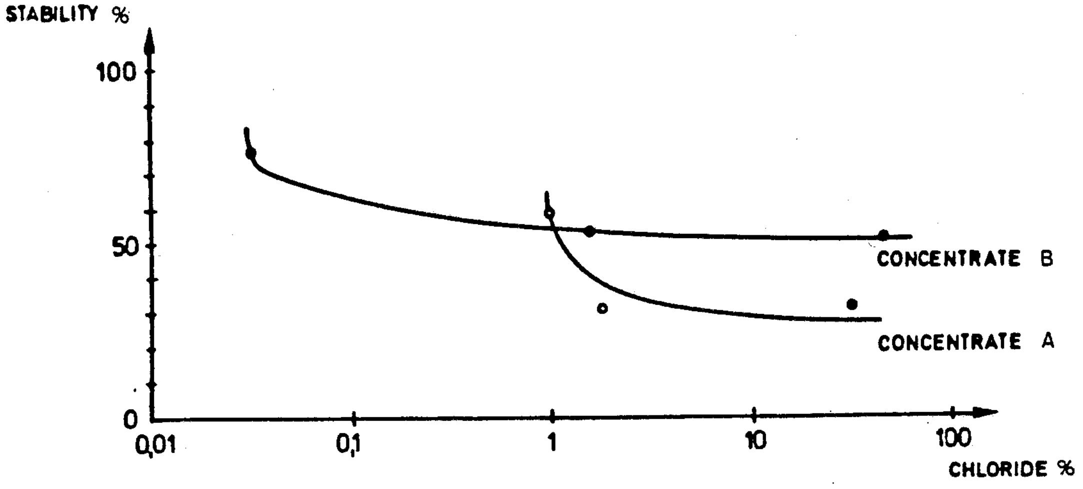

The field of enzymatic detergent additives has been rapidly growing during the last decades. Reference is made to e.g., the article "How Enzymes Got into Detergents", Vol. 12, Developments in Industrial Microbiology, a publication of the Society for Industrial Microbiology, American Institute of Biological Sciences, Washington, D.C. 1971, by Claus Dambmann, Poul Holm, Villy Jensen and Mogens Hilmer Nielsen, and to the article "Production of Microbial Enzymes", Microbial Technology, Sec. Ed., Vol. I, Academic Press, 1979, pp. 281–311, by Knud Aunstrup, Otto Andresen, Edvard A. Falch and Tage Kjaer Nielsen. Inclusion of enzymes in detergent formulations is a long accepted practice.

The most common enzymatic detergent additive is a proteolytic additive, but also amylolytic, cellulolytic, and lipolytic detergent additives are contemplated by the art. See, for example, Great Britain Pat. No. 1,554,482, BE Pat. No. 888,632, and U.S. Pat. No. 4,011,169. Enzymes named above are not an exhaustive listing, but they represent the most common enzymatic additives used in commercial detergent compositions.

This invention is concerned exclusively with enzyme containing granulates used as detergent additives.

One of the most common commercially available forms of an enzymatic additive is the granulate form. For the purposes of this invention, a prilled product is considered a specially prepared granulate. These granulates can be produced in several different ways. Great Britain Pat. No. 1,362,365 describes the production of enzyme containing granulates used as detergent additives by means of an apparatus comprising an extruder and a spheronizer (sold as MARUMERIZER ®), and U.S. Pat. No. 4,106,991, describes the production of enzyme containing granulates used as detergent additives by means of a drum granulator, both patents being incorporated herein by reference.

The granulate enzyme forms supplied by enzyme producers to the detergent industry have achieved market acceptance to such a degree that granulates substantially improved in some major characteristic e.g., in enzyme stability, are not likely to be accepted by the detergent industry if accompanied by any significant level of deterioration in the physical stability of the granule.

The object of this invention is to provide an enzyme containing granulate composition exhibiting improved enzyme stability and, in addition, the physical stability level to which the detergent art has become accustomed.

Other objects of this invention are set forth hereinafter.

RATIONALE OF THIS INVENTION

Typically, the enzymatic ingredient(s) constitute(s) but a small fraction of the enzyme containing granule. The bulk of the granule is comprised of filler materials, granulating aids, binder, etc. (See, for example, the descriptions of granulate compositions provided in the above-referenced patents).

Sodium chloride is a most common filler material for enzyme containing granules, forming a relatively high proportion of the granule weight.

The price is favorable; the granulating process operates very smoothly with sodium chloride (which is not true for some alternative fillers); the physical stability of the finished granulates is satisfactory to the detergent industry. Sodium chloride does not exert any undesired effects in the final washing solution; very small concentrations of salts in the washing solution originate from the granules (as the enzyme containing granule typically constitutes only around 0.5% of the detergent composition).

However, it has now been found that the sodium chloride filler has a serious drawback. Under very high humidity conditions enzyme granulates containing sodium chloride in usual filler concentrations exhibit a low enzyme stability, both when stored as enzyme granulates as such, and subsequent to being mixed into the detergent powder, the latter especially happening when perborate is a component of the detergent powder. It has been found that chloride is the active stability reducing principle, from which it follows that other soluble chlorides, e.g., potassium, ammonium and calcium chloride exert a similar detrimental effect on enzyme stability in granulates of this kind and would serve poorly as alternatives for the sodium chloride filler.

A concentration of chloride of more than around 0.5% w/w, especially more than around 2% w/w in the enzyme containing granulates exert significant detrimental effect on enzyme stability. The present invention has arisen from this discovery. Plots made of enzyme stability versus chloride concentration generated smooth curves. The above given chloride concentration limits of 0.5% and 2% are estimates made by the inventors hereof as pragmatic guidelines for limiting enzyme activity losses to levels acceptable to the detergent art.

Reference is made to the attached drawings wherein:

FIGS. 1–6 constitute semi-logorithmic graphs of enzyme stability versus chloride content for various commercially available enzymes.

It should be appreciated that simply omitting the sodium chloride filler, so as to reduce chloride content to below about 2% w/w, preferably less than about 0.5% w/w, is not enough to produce an enzyme containing granulate useful as a detergent additive. Some other filling material must be substituted, and therein reside considerable difficulties. If the entire amount of chloride filler is substituted for by a different inexpensive water soluble salt, e.g., $Na_2SO_4$, the enzymatic stability problem will be solved, but the granulates have been found to exhibit poor physical stability, which, in turn, might suggest need to then increase the relatively expensive binder components, which, in turn, changes production costs of the granule and may also force changes in production methods. Omission of the sodium chloride filler (without filler substitution) increases the enzyme content of the granulate to an undesirable degree. For example, in UK Pat. No. 1,297,461, Example 3 describes an enzyme granulate filled with sodium tripolyphosphate and calcium sulfate. Extrudability of the mixture is poor, and the physical stability of the resulting granulate is poor.

Manifestly, success in eliminating the sodium chloride filler from the enzyme containing granules heretofore supplied to the soapers may not be achieved casually.

Thus, an additional object of this invention is to provide a filler system that may be employed as a substitute for sodium chloride in enzyme containing granules without detriment to physical stability of the granules.

Another object is to provide an enzyme containing granule of improved enzyme stability with essentially the same physical stability as the sodium chloride filled granules known to the art that may be made with the granulating equipment heretofore used to manufacture enzyme granulates.

BRIEF STATEMENT OF THE INVENTION

According to the invention it has been found that the enzyme containing granulates useful as detergent additives for exhibiting excellent enzyme stability and excellent physical stability can be prepared, if the bulk of the chloride filler is substituted in part by another water soluble salt or a mixture of soluble salts belonging to the category of salts hereinafter defined and in part by one or more water insoluble salts hereinafter defined. The proportion of soluble salt to insoluble salt is important.

Thus, according to the invention the enzyme containing granulates used as detergent additives contain less than about 2% w/w cloride, preferably less than about 0.5% w/w chloride, and contain a filler system which comprises between 5 and 70% w/w of one or more water soluble sulphates of a metal selected from the first group of the periodic table, magnesium sulphate, or ammonium sulphate and between 5 and 70% w/w is one or more water insoluble salt selected from the sulphates, carbonates, phosphates and silicates, whereby the total percentage of the water soluble salt(s) and the water insoluble material in the granulating composition is at least 35% w/w, preferably at least 45% w/w, the balance up to 100% w/w being enzyme, coating materials, granulating aids, water, and impurities, as well as such optional additives as enzyme stabilizers, solubilizing agents, and cosmetic agents.

For practice of this invention, water insolubility can be taken to be a room temperature solubility product K of less than $10^{-3}$, and water solubility can be taken as room temperature solubility of at least 10 grams per liter.

Preferably, the water soluble salt(s) itself is present in the filler system in an amount of 10–65% w/w, more preferably in an amount of 20–60% w/w of the granulate. Typical examples of preferred soluble sulphates for the purpose of this invention are the sulphates of sodium, potassium, ammonium and magnesium, sodium sulphate being particularly preferred.

Preferably, the water insoluble material in the filler system is present in an amount of 5–60% w/w of the granulate.

The chloride content that is permissible in the enzyme-containing granule depends somewhat on the nature of the enzyme; sometimes on the concentrate composition. For the well-known commercially available proteolytic enzyme ALCALASE®, a noticeable enzyme stability decrease can be found in granulates containing around 0.5% w/w chloride content in the granule and a rather remarkable decrease in enzyme stability can be found in granulates containing around 2.0% w/w chloride.

DISCUSSION OF THE INVENTION

For the purposes of this invention the term granulating aids has been employed to include all the agents commonly used to assist the granulation process, e.g., binders and lubricating agents. Reference is made to UK Pat. No. 1,362,365, Page 2, lines 35–57 for details of various granulating aids.

The "impurities" alluded to above, as present in the granulate composition, are the non-enzymatically active materials present in the granule without any function in the granule. They are usually present in the enzyme concentrate component of the granule and originate from the fermentation broth or procedure productive of the enzymes. The cloride content to be found in granulates made according to preferred practice of this invention i.e., no added chloride, constitutes part of the enzyme concentrate. However, chloride from the enzyme concentrate will amount to less than 2% w/w of the granulate, and usually less than 0.5% w/w.

The binder is a necessary component in the enzyme granulates. Conventional binders are contemplated, examples of which are: starch, starch derivatives, starch hydrolysis products and their derivatives (e.g., dextrines), sugars (e.g., dextrose, saccharose, sorbitol), cellulose derivatives (e.g., Na-CMC), gelatine, polyvinyl pyrrolidone, polyvinyl acetate, and polyvinyl alcohol. It has to be taken into account, however, that some binders may have a somewhat adverse effect on enzyme stability and, thus, should be added in relatively small concentration. In preferred embodiment granulates according to the invention, the granulates contain between 1 and 10% w/w of the binder. In this manner, granulates with an excellent physical stability and enzyme stability are obtained.

In a specially preferred embodiment of the granulates according to the invention, the enzyme is a proteolytic enzyme, especially one of the widely used commercial enzymes, ALCALASE®, SAVINASE®, or ESPERASE®. Granulates of these enzymes made according to practice of this invention exhibit both a satisfactory enzyme stability and physical stability.

In a specially preferred embodiment of the granulates according to the invention, the proteolytic activity of the granulates is between 0.5 and 5.0 Anson units/g of granulate. This range is for practical purposes. Enzyme containing granulates of between 0.5 and 5.0 Anson units/g granulate have been found to generate suitable proteolytic activity in the detergent powder, when incorporated therein according to conventional practices.

In a preferred embodiment of the granulates according to the invention, the enzyme is an amylolytic enzyme, and the amylolytic activity of the granulates is between 15 and 400 KNU/g. For practical purposes, it has been found that an amylolytic activity of the granulates between 300 and 300 KNU/g of granulate is most suitable in order to generate the desired amylolytic activity in the detergent powder.

In a preferred embodiment of the granulates according to the invention, the enzyme is the amylolytic enzyme, TERMAMYL®. This is a commercial enzyme and, thus, it is extremely important that granules made therewith exhibit both satisfactory enzyme stability and physical stability.

In a specially preferred embodiment of granulates according to the invention, the granulates are produced by extruding and spheronizing. In this manner, a granulate with excellent physical stability and enzyme stability can be produced inexpensively.

THE FILLER SYSTEM

The lower the concentration of water soluble salt in the granulate, the higher may be the concentration of the insoluble salt in the granulate. However, too high concentration of the insoluble salt, i.e., more than 70% of the granulate w/w, is a drawback to the ultimate dissolution of the enzyme containing granulate into the washing solution.

If the granulates are formulated with more than 70% w/w of the soluble salt, the physical stability of the final granulate generally will be unsatisfactory. Furthermore, in case such granulate is produced by means of a MARUMERIZER®, the granulating process proceeds in an unsatisfactory manner; crumbling has been observed. Crumbling impairs the yield of granulate and creates serious dust problems for the enzyme supplier and for the detergent formulators.

As a practical matter, only $Na_2SO_4$, $K_2SO_4$, $(NH_4)_2SO_4$, and $MgSO_4$ are contemplated for the soluble salts; sulphates of other metals are too expensive.

Examples of insoluble materials are calcium and barium sulphates, calcium, magnesium and barium carbonates, phosphates and silicates. Preferred are calcium carbonate and calcium sulphate.

The soluble and insoluble salts constitute a filler system employed respectively as 5–70 wt % of the granulate. Together they constitute at least 35%, preferably at least 45% by wt of the granulate. These ranges fit all the usual granulation methods, which is to say also, that each standard granulating method will operate best within some narrow portion of the ranges given above. Guidance toward establishing optimum portions of these ranges other than the guidance offered by the specific Examples herein cannot be offered. The salt proportions in this filler system and the quantity of this filler system as a wt % of the granulate can vary with the granulation method, the quantities of other ingredients desired in the granulate, and the weight of coating applied on the granulate. Parenthetically, it is noted that the discussion herein has largely been directed to uncoated granules, since addition of the coating blurs the differences in physical strength of test granulate compositions. A typical prior art coating that may be present in the granulate comprises a mixture of 4 parts titanium dioxide, 1 part magnesium silicate and some polyethylene glycol (PEG) 1500. Persons skilled in the art will be able to correlate the granulation method used to the most suitable proportions of soluble salts, insoluble salts, and appropriate total content in the granulate. The specific Examples herein provided may be looked to as guides for selecting optimum filler amounts and proportions for the filler system.

Therefore, many of the Examples herein provided relate to production of granulates not within the scope of the present invention. Some are posed to illustrate the detrimental effect of chloride concentration on enzyme stability; others to illustrate the level of improvement attainable for granulates made according to practice of this invention.

DETAILED PRACTICE OF THE INVENTION

It is believed that detailed practice of this invention is best presented through provision of a large number of Examples drawn from the experimental effects from which this invention arose.

In most of the Examples concerned with physical stability of the granule, a value of the enzyme stability is indicated separately for each Example. However, as it is a very laborious task to carry out such enzyme stability tests, and as it is desirable to generate an indication of enzyme stability in as many Examples as possible, in some, an enzyme stability value of a granulate not identical to the one of the Example, but quite similar thereto is indicated. As a consequence, the enzyme stability value is indicated on a semi-quantitative basis only, i.e., somewhat better than control (C), much better than control (B), and excellent (A). The control is a similar prior art granulate, in which the soluble and insoluble salts are substituted by an equal amount of NaCl. Also, some of the stability tests are carried out with the granulates per se, and others are carried out with a mixture of the granulates and a detergent, wherein the granulates are present in an amount of 1% w/w of the mixture, and the detergent is a heavy duty standard European powder detergent containing 25% of perborate. In all stability tests, the temperature is 25° C. or 30° C., and the humdiity is 80%.

In regard to the proteolytic activity measurement (Anson units and KNPU units) reference is made to the NOVO publication AF 101/4-GB. In regard to the amylolytic activity measurement (KNU units) reference is made to the NOVO publication F-820385.

Both NOVO publications are available for NOVO INDUSTRI A/S, Novo Alle, 2880 Bagsvaerd, Denmark.

EXAMPLE 1

This Example demonstrates the detrimental effect of chloride on enzymatic stability of protease containing granulates.

All granulates contained the following principal constituents:

10% cellulose Arbocel BC 200
4% $TiO_2$
3% yellow dextrin
25% Alcalase concentrate about 11.5 AU/g
ad 100% salt The ALCALASE® concentrate was produced as indicated in Great Britain Pat. No. 2,078,746A, Page 3, lines 36–45.

The above-indicated salt is a mixture of $Na_2SO_4$ and NaCl in proportion which generates the desired chloride content in the granulate.

The granulates were produced as described in Example 1 in U.S. Pat. No. 4,106,991 (except that no PVP was used), and the coating was performed as described in U.S. Pat. No. 4,106,991, Example 22, except that 7% PEG 4000 and 11.25% titanium dioxide/magnesium silicate 4:1 was used and the temperature during coating was 65° C. (versus 55° C. for PEG 1500).

The granulates were employed as a 1% constituent of a standard European enzyme containing detergent with 25% w/w perborate. The enzyme stability was measured after storage of the detergent at 25° C. and at 30° C., both at 80% relative humidity.

The data is tabulated below. In addition, the data is plotted as FIG. 1 herein so as to provide a visual indication of the dependency between enzyme stability and chloride concentration. FIGS. 2–6 represent plots of the experimental data hereinafter provided in Tables 2–6.

TABLE 1

| FIG. 1 30° C., 80% Relative Humidity | | | | |
|---|---|---|---|---|
| | Granulate Identification | Chloride % | Activity of Alcalase Granulate Used, AU/g | % Residual Activity After 2 Weeks |
| Concentrate A | 10326 | 1.0 | 2.0 | 59 |
| | 10326A | 2.6 | 2.0 | 31 |
| | 10324 | 31.4 | 2.0 | 31 |
| Concentrate B | 10522 | 0.05 | 2.0 | 78 |
| | 10522A | 2.2 | 2.0 | 53 |
| | 10521B1 | 34.1 | 2.0 | 51 |

It appears from Table 1 and FIG. 1 that the dependency between enzyme stability and chloride concentration may be influenced by the nature of the enzyme concentrate. Concentrate A was prepared by salting out. Concentrate B was prepared by an ultrafiltration concentration followed by drying.

TABLE 2

Figure 2:
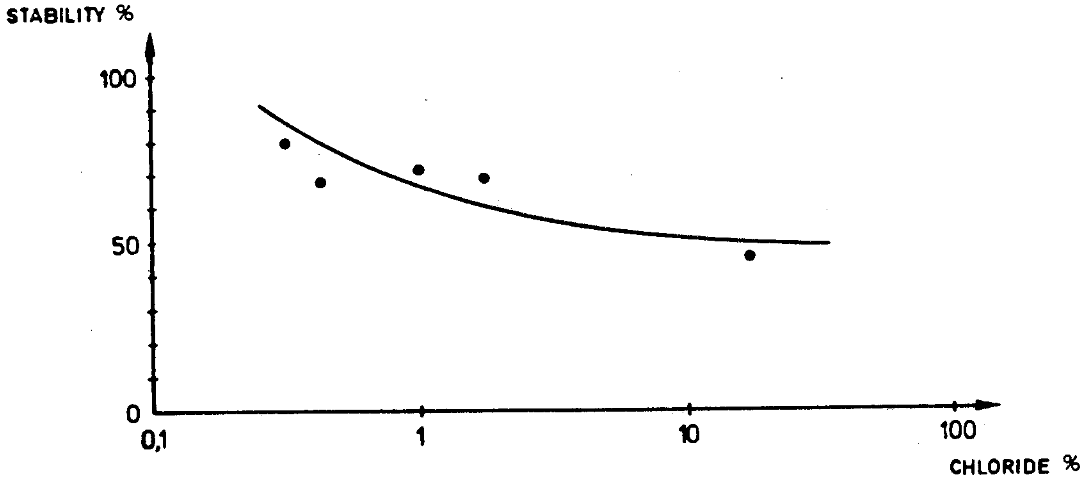

| FIG. 2 25° C., 80% Relative Humidity | | | |
|---|---|---|---|
| Granulate Identification | Chloride % | Activity of Alcalase Granulate Used, AU/g | % Residual Activity After 2 Weeks |
| 30929 | 0.4 | 2.0 | 80 |
| 31006 | 0.6 | 2.0 | 68 |
| 31013 | 1.0 | 2.0 | 72 |
| 31013A | 1.4 | 2.0 | 69 |
| 31014 | 29 | 2.0 | 45 |

EXAMPLE 2

This Example demonstrates the detrimental effect on enzymatic stability of high chloride concentration in amylase-containing granulates used as detergent additives.

A TERMAMYL® concentrate produced by cultivation of *Bacillus licheniformis* was produced as described in Canada Pat. No. 964,215, reference being especially made to the paragraphs bridging Pages 5 and 6. The granulate was produced according to Example 1 of U.S. Pat. No. 4,106,991.

The granulates were employed as a 1% constituent of a standard European detergent with 25% w/w perborate. The enzyme stability was measured after storage at 25° C. and 80% relative humidity.

TABLE 3

Figure 3:
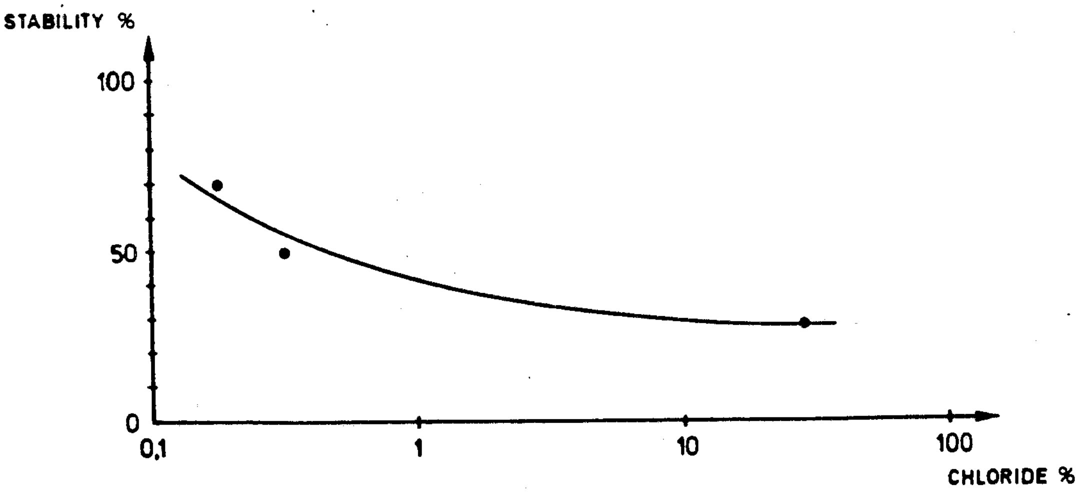

| FIG. 3 25° C., 80% Relative Humidity | | | |
|---|---|---|---|
| Granulate Identification | Chloride % | Activity of Termamyl Granulate Used, KNU/g | % Residual Activity After 2 Weeks |
| 31005Z | 0.3 | 60 | 70 |
| 31006Z | 0.5 | 60 | 50 |
| 31004Y | 38 | 60 | 24 |

EXAMPLE 3

Experiments with increasing amount of different chlorides were carried out with proteinease containing granulates prepared by means of extrusion and spheronizing on a MARUMERIZER, similarly to Example 4 and it was found that the detrimental effect of the chlorides, increasing with the concentration of the chlorides, was independent of the cation of the chloride.

The temperature during the stability test was 25° C., and the humidity was 80%.

The results appear from the following Tables.

TABLE 4

Figure 4:
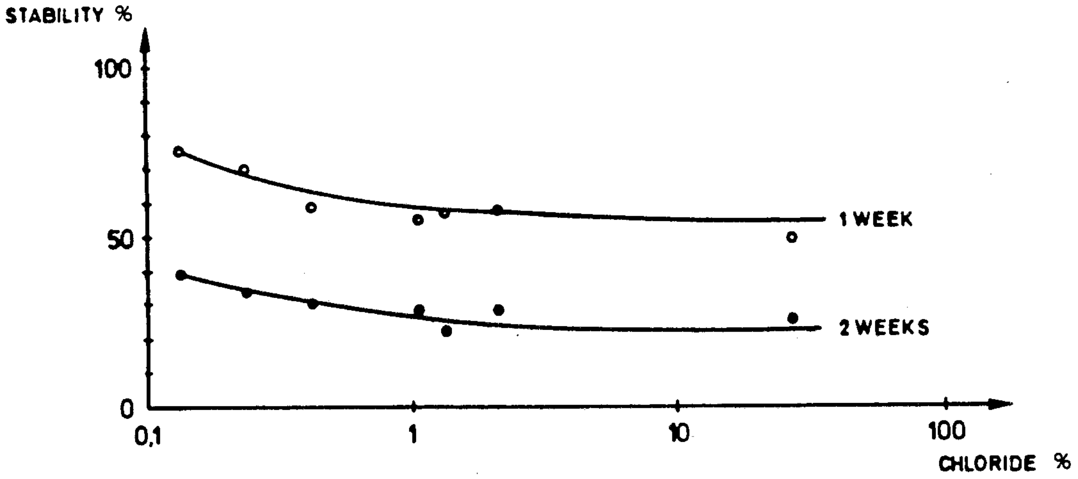

| FIG. 4 SAVINASE M Granulate, Initial Activity 6.0 KNPU/g | | | |
|---|---|---|---|
| Granulate Identification | Chloride % (Added as $CaCl_2$) | Residual Activity After 1 Week | Residual Activity After 2 Weeks |
| 41121 | 0.29 | 76 | 39 |
| 41127 | 0.49 | 60 | 34 |
| 41127A | 0.69 | 59 | 30 |
| 41127B | 1.1 | 55 | 28 |
| 41127C | 1.9 | 57 | 22 |
| 41127D | 3.5 | 58 | 28 |
| 41122D | 35.0 | 49 | 25 |

TABLE 5

Figure 5:
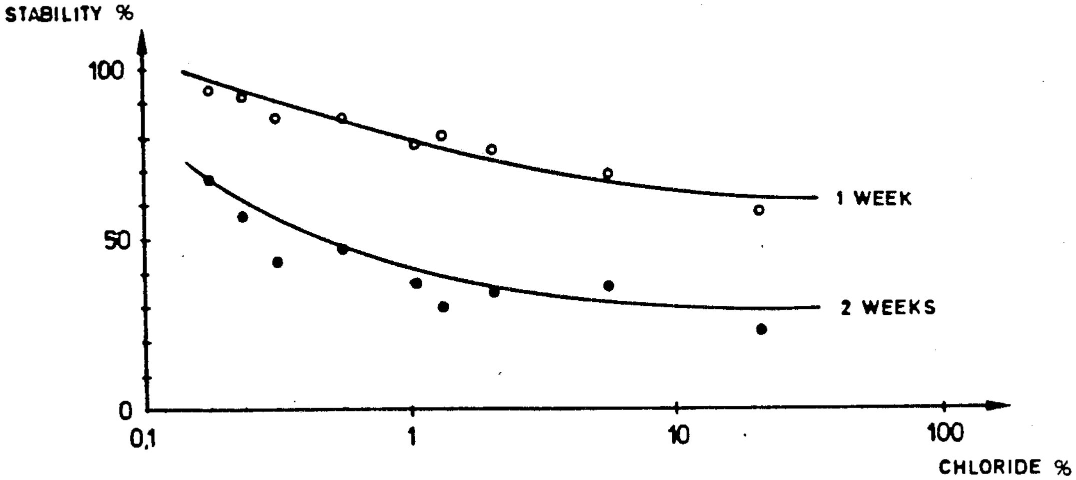

| FIG. 5 ALCALASE M Granulate, Initial Activity 2.0 Anson Units/g | | | |
|---|---|---|---|
| Granulate Identification | Chloride % (Added as KCl) | Residual Activity After 1 Week | Residual Activity After 2 Weeks |
| 41126 | 0.28 | 94 | 68 |
| 41126A | 0.38 | 92 | 57 |
| 41126B | 0.49 | 86 | 44 |
| 41126C | 0.71 | 86 | 47 |
| 41126D | 1.1 | 78 | 37 |
| 41126E | 2.0 | 80 | 30 |
| 41126F | 3.6 | 76 | 34 |
| 41126G | 7.2 | 69 | 36 |
| 41126H | 25.8 | 58 | 23 |

TABLE 6

Figure 6:
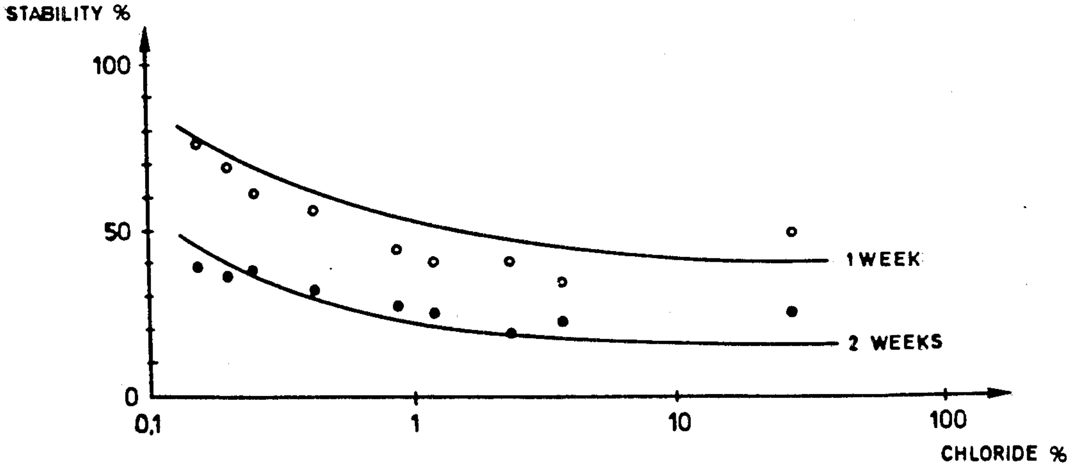

| FIG. 6 SAVINASE M Granulate, Initial Activity 6.0 KNPU/g | | | |
|---|---|---|---|
| Granulate Identification | Chloride % (Added as $NH_4Cl$) | Residual Activity After 1 Week | Residual Activity After 2 Weeks |
| 41121 | 0.25 | 76 | 39 |
| 41121A | 0.34 | 69 | 36 |
| 41121B | 0.42 | 61 | 38 |
| 41121C | 0.598 | 56 | 32 |
| 41122 | 0.92 | 44 | 27 |
| 41122A | 1.6 | 40 | 25 |
| 41122B | 2.9 | 40 | 19 |
| 41122C | 5.6 | 34 | 22 |
| 41122D | 35.0 | 49 | 25 |

EXAMPLES 4–61

In these Examples the enzyme is variously ALCALASE®, SAVINASE® or ESPERASE®, the latter two being commercially available proteolytic enzymes whose production is described in U.S. Pat. No. 3,723,250. The enzyme concentrates are prepared like the ALCALASE® concentrate.

The same granulate fabricating procedure was followed in Examples 4–61, which expressed in typical proportions and batch size, is to produce 7 kg of uncoated granulate after drying by mixing:

0.95 kg of SAVINASE® concentrate (76.4 KNPU/g)

0.14 kg of $TiO_2$ 0.21 kg yellow dextrin 5.28 kg finely ground $Na_2SO_4$ carefully on a 20 l Lodige mixer provided with a mantel for steam heating. The temperature of the powder mixture is raised to 70° C. by introduction of steam in the mantle. Subsequently, the steam is displaced by hot water (temperature 60° C.) in order to keep the feed temperature on a value not below 55°-60° C.

The hot powder mixture is sprayed with a solution consisting of 0.14 kg of polyvinyl pyrrolidon (PVP K 30) in 0.6 kg of water. Finally, the moist powder mixture is sprayed with 0.28 kg of melted coconut monoethanolamide (CMEA).

The above described mixture is transferred to a twin screw extender (Fuji Denki Kogyo, type EXDC-100), in which the mixture is extruded through a 0.8 mm screen.

After extruding the plastic, moist extrudate is transferred to a Marumerizer spheronizer (Fuji Denki Kogyo, type Q-400), in which spheronizing takes place. Then the granulate is dried in a fluid bed apparatus.

The dry granulate is sieved, whereby particles above 1000 u and below 300 u are removed. 2 kg of granulate with a particle size between 300 and 1000 u is coated as indicated in Example 22 in U.S. Pat. No. 4,106,991 in a 5 l Lodige mixer with 4.5% PEG 1500 and 8.5% mixture of titanium dioxide and magnesium silicate (proportion 4:1).

The actual materials and proportions employed in Examples 4-61 are shown in the following Table, along with the results from Examples 4"61. In the study from which Examples 5 and 6 were drawn, 50 Kg each of granulates were produced.

For further details regarding preparation of the granulates, reference is made to Great Britain Pat. No. 1,362,365.

The test for mechanical strength is performed in the following manner. 50 g of sieved granulate with particle size 420-710 u is treated for five minutes in a ball mill (steel cylinder 11.5 cm, height 10 cm) rotating with a velocity of 100 rpm. The cylinder contains 8 steel balls with a diameter of 20 mm. After this treatment, the granulate is sieved again on the 420 u sieve. The mechanical strength is expressed as the percentage of granulate left on the 420 u sieve in relation to the weight of the original sample. Thus, a mechanical strength of e.g., 90% shows that 10% of the granulate is crushed and is able to pas the 420 u sieve by renewed screening. Empirically, it has been found that a physical strength above 90% is necessary if the granulate is to be classified as fully acceptable, i.e., if the granulate can be coated and thereby provide a coated granulate with satisfactory handling properties. A physical strength below 80% is usually considered fully unacceptable in commercial practice.

| | | Core formulation, % (uncoated granulate) | | | | | | | | |
|---|---|---|---|---|---|---|---|---|---|---|
| Example No. | Enzyme Granulate activity, KNPU/g | Concentrate | $TiO_2$ | CMEA | Yellow dextr. | PVP K30 | dextrose monohydrate | $Na_2SO_4$ water soluble salt | *$CaCO_3$ water insoluble salt | **$CaSO_4$ $2H_2O$ water insoluble salt |
| | SAVINASE conc. | | | | | | | | | |
| 4 | 8.0 | 13.6 | 2 | 4 | 3 | 2 | | 75.4 | | |
| 5 | 8.0 | 13.6 | 2 | 4 | 3 | 2 | | 65.4 | 10 | |
| 6 | 8.0 | 13.6 | 2 | 4 | 3 | 2 | 2.5 | 62.9 | 10 | |
| 7 | 4.0 | 6.8 | 2 | 4 | 3 | 2 | | 82.8 | | |
| 8 | 4.0 | 6.8 | 2 | 4 | 3 | 2 | | 6.7 | | 75.5 |
| 9 | 4.0 | 6.8 | 2 | 4 | 3 | 2 | | 44.4 | | 37.8 |
| 10 | 4.0 | 6.8 | 2 | 4 | 3 | 2 | 2.5 | 70.2 | | 9.5 |
| | ESPERASE conc. | | | | | | | | | |
| 11 | 4.0 | 18.5 | 2 | 4 | 3 | 2 | | 70.5 | | |
| 12 | 4.0 | 18.5 | 2 | 4 | 3 | 2 | | 60.5 | 10 | |
| 13 | 4.0 | 18.5 | 2 | 4 | 3 | 2 | 3 | 57.5 | 10 | |
| 14 | 4.0 | 18.5 | 2 | 6 | 7 | 2 | | 24.5 | 40 | |

| Example No. | ***Humidification water, % | Physical strength of uncoated granulate | % of water soluble salt ($Na_2SO_4$) in finished granulate | % of water insoluble salt ($CaCO_3$ or $CaSO_4$ $2H_2O$) in finished granulate |
|---|---|---|---|---|
| 4 | 8.6 | 79 | 66.7 | 0 |
| 5 | 8.9 | 90 | 57.8 | 8.8 |
| 6 | 7.0 | 95 | 55.7 | 8.8 |
| 7 | 7.0 | **** | 73.3 | 0 |
| 8 | 9.0 | 93 | 5.9 | 66.8 |
| 9 | 8.0 | 85 | 39.3 | 33.5 |
| 10 | 8.0 | 98 | 62.1 | 8.4 |
| 11 | 7.5 | 60 | 62.4 | 0 |
| 12 | 7.5 | 80 | 53.5 | 8.8 |
| 13 | 7.5 | 91 | 50.9 | 8.8 |
| 14 | 9.4 | 97 | 21.7 | 35.4 |

*Precipitated calcium carbonate STURCAL type L dm ~ 8μ, mainly below 30μ
**Giulini Chemie Gmbh dm ~ 12μ, mainly below 50μ
***Humidification calculated on uncoated granulate (kept "outside" formulation as the water is removed later during drying)
****Operational performance very poor. Lumps in Marumerizer.

| | | Core formulation, % uncoated granulate - |
|---|---|---|
| Ex- | Enzyme: | water |

-continued

| am-ple No. | SAVINASE Concentrate identification | Strength of granulate, KNPU/g | Concentrate | $TiO_2$ | CMEA | Yellow dextrin | PVP K30 | $Na_2SO_4$ | insoluble salts $CaCO_3$ | $CaSO_4$, $2H_2O$ | Mg Silicate | Aerosil 200 |
|---|---|---|---|---|---|---|---|---|---|---|---|---|
| 30 | 025 | 6.0 | 20 | 2 | 4 | 3 | 2 | 52 | 10 | 7 | | |
| 31 | 025 | 6.0 | 20 | 2 | 4 | 3 | 2 | 49 | 10 | 7 | | 0.5 |
| 32 | 025 | 6.0 | 20 | 2 | 4 | 3 | 2 | 50 | 10 | | 5 | |
| 33 | 025 | 6.0 | 20 | 2 | 4 | | 2 | 52 | 10 | | 5 | |
| 34 | 025 | 8.0 | 27.1 | 2 | 4 | 3 | 2 | 61.9 | | | | |
| 35 | 075 | 6.0 | 21.4 | 2 | 4 | 3 | 2 | 67.6 | | | | |
| 36 | 075 | 6.0 | 21.4 | 2 | 4 | 3 | 2 | 50.6 | 10 | 7 | | |
| 37 | 075 | 6.0 | 21.4 | 2 | 4 | 3 | 2 | 57.6 | 10 | | | |
| 38 | 075 | 6.0 | 21.4 | 2 | 4 | 3 | 2 | 47.6 | 10 | 7 | | 1 |
| 39 | 075 | 6.0 | 21.4 | 2 | 4 | | 2 | 54.6 | 10 | | | |
| 40 | 075 | 6.0 | 21.4 | 2 | 4 | | 2 | 53.6 | 10 | | | |
| 41 | 075 | 6.0 | 21.4 | 2 | 7 | 5 | 2 | 22.6 | 40 | | | |
| 42 | 075 | 6.0 | 21.4 | 2 | 7 | 3 | 2 | 22.6 | 40 | | | |
| 43 | 075 | 6.0 | 21.4 | 2 | 4 | 3 | 2 | 27.6 | | 40 | | |
| 44 | 075 | 6.0 | 21.4 | 2 | 4 | 3 | 2 | 25.6 | | 40 | | |
| 45 | 075 | 6.0 | 21.4 | 2 | 4 | 3 | 2 | 54.6 | 10 | | | |

| Ex-am-ple No. | Core formulation, % uncoated granulate Granulating aids Dextrose monoh. | Saccharose | Amylogum | Na—ascorbate | Gelatine | Na—CMC | Humidification water, % | % of water soluble salt in coated granulate | % of water insoluble salt in coated granulate | Evaluation Physical strength | Suitability for production | Storage stability In detergent | Without detergent |
|---|---|---|---|---|---|---|---|---|---|---|---|---|---|
| 30 | | | | | | | 9.7 | 46.0 | 15.0 | 95 | + | | A |
| 31 | 2.5 | | | | | | 7.0 | 43.4 | 15.5 | 97 | + | | A/B |
| 32 | 4 | | | | | | 8.9 | 44.2 | 13.2 | 96 | + | | B |
| 33 | | | 5 | | | | 15.9 | 46.0 | 13.2 | 92 | + | | A |
| 34 | | | | | | | 8.6 | 54.7 | 0 | 79 | + | | A |
| 35 | | | | | | | 7.5 | 59.8 | 0 | 83 | (+) | | A |
| 36 | | | | | | | 8.6 | 44.8 | 15.0 | 94 | + | | A |
| 37 | | | | | | | 8.6 | 51.0 | 8.8 | 97 | + | | |
| 38 | | | | 2 | | | 9.0 | 42.1 | 15.9 | 98 | + | | |
| 39 | | 1 | 5 | | | | 10.9 | 48.3 | 8.8 | 98 | + | | A |
| 40 | | 2 | 5 | | | | 10.0 | 47.9 | 8.8 | 95 | + | | A |
| 41 | | | | | | | 9.4 | 20.0 | 35.4 | 96 | + | | |
| 42 | | 2 | | | | | 8.4 | 20.0 | 35.4 | 94 | + | | |
| 43 | | | | | | | 8.0 | 24.4 | 35.4 | 97 | + | | |
| 44 | | 2 | | | | | 8.0 | 22.7 | 35.4 | 97 | + | | |
| 45 | | | | | 2 | 1 | 10.0 | 48.3 | 8.8 | 95 | + | | |

| Ex-am-ple No. | Enzyme: SAVINASE Concentrate identification | Activity of granulate, KNPU/g | Core formulation, % uncoated granulate Concentrate | $TiO_2$ | CMEA | Yellow dextrin | PVP K30 | $Na_2SO_4$ | water insoluble salts $CaCO_3$ | $CaSO_4$, $2H_2O$ | Mg Silicate | Aerosil 200 |
|---|---|---|---|---|---|---|---|---|---|---|---|---|
| 15 | 008 | 4.0 | 15.7 | 2 | 4 | 3 | 2 | 73.3 | | | | |
| 16 | 008 | 4.0 | 15.7 | 2 | 4 | 3 | 2 | 73.3 | | | | |
| 17 | 008 | 4.0 | 15.7 | 2 | 4 | 3 | 2 | 73.3 | | | | |
| 18 | 008 | 6.0 | 24.2 | 2 | 4 | 3 | 2 | 64.7 | | | | |
| 19 | 008 | 8.0 | 31.2 | 2 | 4 | 3 | 2 | 67.6 | | | | |
| 20 | 012 | 6.0 | 15.2 | 2 | 4 | 3 | 2 | 73.3 | | | | |
| 21 | 012 | 6.0 | 15.2 | 2 | 4 | 3 | 2 | 62.3 | 10 | | | |
| 22 | 012 | 6.0 | 15.2 | 2 | 4 | 3 | 2 | 53.8 | 10 | 7 | | |
| 23 | 012 | 8.0 | 24.3 | 2 | 4 | 3 | 2 | 64.7 | | | | |
| 24 | 012 | 8.0 | 24.3 | 2 | 4 | 3 | 2 | 44.7 | 20 | | | |
| 25 | 012 | 8.0 | 24.3 | 2 | 6 | 5 | 2 | 40.7 | 20 | | | |
| 26 | 030 | 4.0 | 17.1 | 2 | 4 | 3 | 2 | 71.9 | | | | |
| 27 | 030 | 4.0 | 17.1 | 2 | 4 | 3 | 2 | 59.1 | 10 | 7 | | 0.5 |
| 28 | 030 | 4.0 | 17.1 | 2 | 4 | 3 | 2 | 53.1 | 10 | 7 | | 0.5 |
| 29 | 030 | 4.0 | 17.1 | 2 | 4 | 3 | 2 | 51.4 | 10 | 7 | | 1 |

| Ex-am-ple No. | Core formulation, % uncoated granulate Granulating aids Acdisol | Sorbitol | Dextrose monoh. | Saccharose | Amylogum | Humidification water, % | % of water soluble salt in coated granulate | % of insoluble salt in coated granulate | Evaluation Physical strength | Suitability for production | Storage stability In detergent | Without detergent |
|---|---|---|---|---|---|---|---|---|---|---|---|---|
| 15 | | | | | | 7.1 | 64.9 | 0 | 89 | – | A | |
| 16 | | | | | | 7.5 | 64.9 | 0 | 88 | – | A | |
| 17 | | | | | | 6.0–9.0 | 64.9 | 0 | — | – | A | |
| 18 | | | | | | 11.6 | 67.3 | 0 | 82 | + | A | |
| 19 | | | | | | 13.3 | 51.0 | 0 | 77 | + | A | |
| 20 | | | | | | 7.5 | 64.9 | 0 | 82 | + | A | A |
| 21 | 1 | | | | | 11.4 | 65.1 | 8.8 | 98 | + | | A |
| 22 | | 2.5 | | | | 7.5 | 17.6 | 15.0 | 97 | + | | B |

-continued

| | | | | | | | | | | |
|---|---|---|---|---|---|---|---|---|---|---|
| 23 | | | | 9.3 | 57.3 | 0 | 67 | (+) | A | A |
| 24 | | | | 8.9-10 | 39.6 | 17.7 | 91-86 | + | B | |
| 25 | | | | 9.0 | 36.0 | 17.7 | 98 | + | B | |
| 26 | | | | 7.5 | 63.6 | 0 | 97 | – | | A |
| 27 | | 1.25 | | 7.5 | 17.0 | 15.5 | 98 | (+) | | A/B |
| 28 | 1.25 | | | 7.1 | 17.0 | 15.5 | 98 | (+) | | B |
| 29 | | | 2.5 | 9.5 | 45.5 | 15.9 | 97 | + | A | |

| Example No. | Enzyme: ALCALASE Concentrate identification | Enzyme: ALCALASE Granulate act. 2.0 AU/g | Core formulation, % uncoated granulate: Concentrate | $TiO_2$ | CMEA | Yellow dextrin | PVP K30 | $Na_2SO_4$ | water insoluble salts: $CaCO_3$ | $CaSO_4$, $2H_2O$ | Mg Silicate | Aerosil 200 |
|---|---|---|---|---|---|---|---|---|---|---|---|---|
| 46 | 151 | 2.0 | 22.9 | 2 | 6 | 5 | 2 | 62.1 | | | | |
| 47 | 151 | 2.0 | 22.9 | 2 | 6 | 5 | 2 | 52.1 | 10 | | | |
| 48 | 151 | 2.0 | 22.9 | 2 | 4 | 3 | 2 | 53.1 | 10 | | | |
| 49 | 151 | 2.0 | 22.9 | 2 | 6 | 5 | 2 | 28.1 | 34 | | | |
| 50 | 151 | 2.0 | 22.9 | 2 | 6 | 5 | 2 | 26.1 | 31 | | | |
| 51 | 206 | 2.0 | 22.9 | 2 | 6 | 5 | 2 | 62.1 | | | | |
| 52 | 206 | 2.0 | 22.9 | 2 | 6 | 5 | 2 | 52.1 | 10 | | | |
| 53 | 206 | 2.0 | 22.9 | 2 | 6 | 5 | 2 | 50.1 | 10 | | | |
| 54 | 206 | 2.0 | 22.9 | 2 | 4 | 3 | 2 | 54.1 | 10 | | | |
| 55 | 044 | 2.0 | 24.3 | 2 | 6 | 5 | 2 | 60.7 | | | | |
| 56 | 044 | 2.0 | 24.3 | 2 | 4 | 3 | 2 | 60.7 | | | | |

| Example No. | Core formulation, % uncoated granulate, Granulating aids: Dextrose | Na—ascorbate | Humidification water, % | % of water soluble salt in coated granulate | % of water insoluble salt in coated granulate | Evaluation: Physical strength | Suitability for production | Storage stability: In detergent | Without detergent |
|---|---|---|---|---|---|---|---|---|---|
| 46 | | | 7.0 | 55.0 | 0 | 67 | + | A | |
| 47 | | | 10.0 | 46.1 | 8.8 | 97 | + | B | |
| 48 | 3 | | 7.0 | 47.0 | 8.8 | 96 | + | B | |
| 49 | | | 11.0 | 24.9 | 30.1 | 84 | + | A/B | |
| 50 | 5 | | 7.4 | 23.1 | 27.4 | 95 | + | A/B | |
| 51 | | | 9.0 | 55.0 | 0 | 89 | + | | A |
| 52 | | | 8.7 | 46.1 | 8.8 | 91 | + | A | |
| 53 | | 2 | 9.4 | 44.3 | 8.8 | 98 | + | A | |
| 54 | | 2 | 10.0 | 47.9 | 8.8 | 93 | + | A | |
| 55 | | | 7.1-8.6 | 53.7 | 0 | 77-85 | + | A | |
| 56 | | | 10.8-12.0 | 57.3 | 0 | 29-71 | + | A | |

| Example No. | Enzyme: ESPERASE Concentrate identification | Enzyme: ESPERASE Strength of granulate, KNPU/g | Core formulation, % uncoated granulate: Concentrate | $TiO_2$ | CMEA | Yellow dextrin | PVP K30 | $Na_2SO_4$ | water insoluble salts: $CaCO_3$ | $CaSO_4$, $2H_2O$ | Mg Silicate | Aerosil 200 |
|---|---|---|---|---|---|---|---|---|---|---|---|---|
| 57 | 194 | 4.0 | 12.9 | 2 | 6 | 3 | 2 | 74.1 | | | | |
| 58 | 194 | 4.0 | 12.9 | 2 | 6 | 3 | 2 | 64.1 | 10 | | | |
| 59 | 194 | 4.0 | 12.9 | 2 | 6 | 3 | 2 | 57.1 | 10 | 7 | | |
| 60 | 194 | 4.0 | 12.9 | 2 | 6 | 3 | 2 | 54.6 | 10 | 7 | | |
| 61 | 194 | 4.0 | 12.9 | 2 | 6 | 3 | 2 | 61.6 | 10 | | | |

| Example No. | Core formulation, % uncoated granulate, Granulating aids: Dextrose monoh. | Saccharose | Humidification water, % | % of water soluble salt in coated granulate | % of water insoluble salt in coated granulate | Evaluation: Physical strength | Suitability for production | Storage stability: In detergent | Without detergent |
|---|---|---|---|---|---|---|---|---|---|
| 57 | | | 4.6 | 65.6 | 0 | 76 | – | A/B | |
| 58 | | | 6.0 | 56.7 | 8.8 | 69 | + | | |
| 59 | | | 8.0 | 50.5 | 15.0 | 84 | + | | |
| 60 | 2.5 | | 7.0 | 48.3 | 15.0 | 91 | + | | |
| 61 | | 2.5 | 5.7 | 54.5 | 8.8 | 94 | + | | |

We claim:

1. In the process for granulating an enzyme composition comprising enzyme, inorganic water soluble salts and a granulation binder, the improvement which comprises incorporating into the composition: less than 2% w/w chloride and from 5 to 70% w/w of a water insoluble salt selected from the group consisting of inorganic water insoluble sulphates, carbonates, phosphates and silicates; and employing for the water soluble inorganic salts, one or more water soluble sulphates from the group consisting of ammonium sulphate, magnesium sulphate, and sulphates of metals from the first group of the periodic Table, in content of 5 to 70% w/w, the total salts content exceeding about 35% w/w of the granulate composition.

2. The process of claim 1 further comprising forming the granulate by extruding and spheronizing.

3. The process of claim 1 wherein the chloride content is below about 0.5% w/w in said composition.

4. Enzyme containing granulates adapted for detergent additive purposes containing therein less than about 2% chloride by weight thereof, enzyme, a granulation binder, and at least 35% by weight of a filler system comprising at least one water insoluble salt selected from the group consisting of inorganic water insoluble sulphates, carbonates, phosphates and silicates, and at least one water soluble inorganic salt selected from the group consisting of the sulphates of ammonium, magnesium and metals from the first group of the periodic Table, said water soluble salt and water insoluble salt each being present as from 5% to 70% by weight of the granulates.

5. The granulates of claim 4 containing therein less than about 0.5% chloride by weight.

6. The granulates of claim 4 containing binder in 1–10% by weight of the granulates.

7. The granulates of claim 4 wherein the enzyme comprises a proteinase.

8. The granulates of claim 4 wherein the enzyme comprises the proteinase from *Bacillus licheniformis* and the proteolytic activity of the granulate is between 0.5 and 5.0 Anson units/g of granulate.

9. The granulates of claim 4 wherein the soluble salts are from the group of $Na_2SO_4$; $K_2SO_4$, $(NH_4)_2SO_4$.

10. The granulates of claim 4 wherein the water insoluble salts are selected from the group consisting of calcium and barium sulphates, and calcium, magnesium and barium carbonates, phosphates and silicates.

11. The granulates of claim 4 wherein the enzyme is an amylolytic enzyme and the amylolytic activity is between 15 and 400 KNU/g of the granulate.

12. The granulates of claim 4 wherein sodium sulphate is the water soluble salt and comprises 20–60% w/w of the granulate.

13. The granulates of claim 11 wherein the water insoluble salt is calcium carbonate or calcium sulphate and comprises 5–40% w/w of the granulate.

* * * * *